United States Patent [19]

Terasaka

[11] Patent Number: 4,782,690
[45] Date of Patent: Nov. 8, 1988

[54] AIR/FUEL RATIO DETECTING APPARATUS, AND METHOD OF DETECTING NORMAL AND ABNORMAL CONDITIONS OF THE SENSOR

[75] Inventor: Katsunori Terasaka, Yokosuka, Japan

[73] Assignee: Nissan Motor Co., Ltd., Yokohama, Japan

[21] Appl. No.: 886,067

[22] Filed: Jul. 16, 1986

[30] Foreign Application Priority Data

Jul. 17, 1985 [JP] Japan ............................ 60-110399[U]

[51] Int. Cl.[4] .......................................... G01M 15/00
[52] U.S. Cl. .................................................... 73/116
[58] Field of Search ................ 73/119 A, 117.3, 116; 123/494; 364/431.05

[56] References Cited

U.S. PATENT DOCUMENTS 4,391,130  7/1983  Nakano et al. ................. 73/117.3
4,706,633 11/1987  Nakagawa ........................ 123/491
4,707,241 11/1987  Nakagawa et al. .............. 204/406

FOREIGN PATENT DOCUMENTS 59-46305  3/1984  Japan .
59-67455  4/1984  Japan .

Primary Examiner—Jerry W. Myracle
Attorney, Agent, or Firm—Foley & Lardner, Schwartz, Jeffery, Schwaab, Mack, Blumenthal & Evans

[57] ABSTRACT

An air/fuel ratio sensor having a sensor section and a pump section, capable of accurately sensing air/fuel ratio and an air/fuel ratio detecting and controlling apparatus by utilizing the air/fuel ratio sensor in which the accuracy of air/fuel ratio detection and control can be improved by varying the number of cylinders into which fuel is injected in a multi-step manner, during engine deceleration while maintaining the amount of fuel injected into each cylinder at a constant level, by determining whether the air/fuel ratio sensor operation is normal or abnormal on the basis of the air/fuel ratio sensor output level when fuel injection is performed into all of the cylinders, the output sensor level when fuel injection is performed only into specific cylinders, and the sensor output level when fuel injection to all cylinders is halted.

A method of detecting an abnormal condition of the air/fuel ratio sensor is also disclosed and a suitable correction of the air/fuel ratio is also performed in accordance with the result of the conditions of the sensor.

18 Claims, 11 Drawing Sheets

AIR/FUEL RATIO DETECTING APPARATUS, AND METHOD OF DETECTING NORMAL AND ABNORMAL CONDITIONS OF THE SENSOR

BACKGROUND OF THE INVENTION (1) Field of the Invention

The present invention relates to an air/fuel ratio sensor, an air/fuel ratio detecting and controlling apparatus, and a method of detecting normal and abnormal conditions of the sensor, capable of accurately detecting and controlling air/fuel ratio.

(2) Description of the Prior Art

In recent years, feedback control of the air/fuel ratio engines has come into use in order to improve the operating characteristics and to lower fuel consumption.

Examples of air/fuel ratio sensors for use in such feedback control are disclosed for example in Japanese Patent Disclosure Nos. 59-67455 and 59-46305. Such air/fuel ratio sensors are generally referred to as being of oxygen-sensing type, in which an amount of oxygen which diffuses between electrodes expresses an oxygen concentration, with this amount of diffusing oxygen being detected as a diffusion current (pump current). In this way the oxygen concentration (air/fuel ratio) can be detected. The pump current flows through an oxygen sensor which is mounted within the exhaust path of the engine, to sense the concentration of oxygen in the exhaust gas, and the air/fuel ratio is detected from the value of this current. More specifically, oxygen molecules which are ionized by the action of a pump cathode are pumped through a solid electrolyte to a pump anode, and the resultant ion current (pump current) is used to detect the concentration of oxygen in the exhaust gas. The air/fuel ratio is correlated with this oxygen concentration.

With such a prior art type of air fuel ratio detection apparatus, insufficient means are available for counteracting the effects of deterioration of the air/fuel ratio sensor and changes in the sensor characteristics over a long period of time. As a result, as time elapses, the sensitivity of detection of the air/fuel ratio decreases and this can result in a lowering of the degree of control of the engine air/fuel ratio. For example, if an oxygen sensor as described above is used as the air/fuel ratio sensor, then due to deterioration of the pump anode over a long period of time, deterioration of the pumping action of the solid electrolyte, or a lowering of the diffusion factor of the diffusion layer, the correlation between the sensor output and the oxygen concentration in the exhaust gas will change. The detection accuracy will thereby be lowered. In addition, if carbon becomes deposited between the electrodes, leakage current will flow and this will also contribute to lowering of the detection accuracy.

Figure 1:
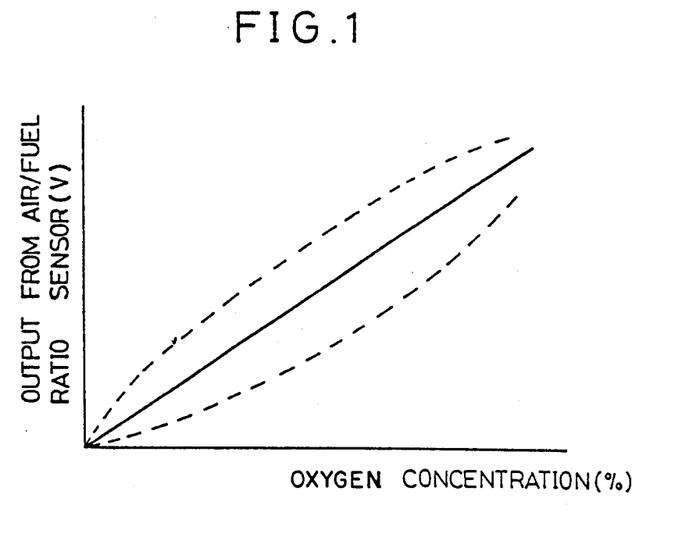
FIG. 1 is the output characteristic of the air/fuel ratio sensor according to the prior art.

FIG. 1 illustrates the changes which can thereby result in the output characteristic of an air/fuel ratio sensor, i.e. non-linearity of the characteristic, as indicated by the broken-line portion. In such a case, even if correction of the air/fuel ratio sensor is performed for the case of exhaust gas having a high concentration of oxygen, satisfactory correction overall will not be possible. As a result, it will not be possible to detect the air/fuel ratio accurately, so that it will not be possible to control the air/fuel ratio precisely to a desired target value.

SUMMARY OF THE INVENTION

It is therefore an object of the present invention to provide an air/fuel ratio sensor which can accurately detect air/fuel ratio of cylinders.

It is another object of the present invention to provide an air/fuel ratio detecting and controlling apparatus in which deterioration of an air/fuel ratio sensor can be detected, as well as realizing accurate detection of the air/fuel ratio.

It is still another object of the present invention to provide air/fuel ratio detecting and controlling method and apparatus in which normal and abnormal conditions of the sensor can be detected and when the sensor is found to be normal, appropriate correction of the air/fuel ratio to a fuel injector can be made.

It is still another object of the present invention to provide an air/fuel ratio detecting and controlling apparatus in which the accuracy of air/fuel ratio detection and control can be improved by varying the number of cylinders into which fuel is injected, in a multi-step manner, during engine deceleration, while maintaining the amount of fuel injected into each cylinder at a constant level, and by judging whether the air/fuel ratio sensor operation is normal or abnormal on the basis of the air/fuel ratio sensor output level when fuel injection is performed into all of the engine cylinders, the sensor output level when fuel injection is performed only into specific cylinders, and the sensor output level when fuel injection to all cylinders is halted.

One feature of the present invention resides in an air/fuel ratio sensor which comprises: a substrate having a heater provided thereon; an air induction plate having an air induction section and provided on the substrate; a first solid electrolyte as a sensor section, having an anode electrode provided on one surface of the first solid electrolyte and a cathode electrode provided on the other surface of the electrolyte face-to-face each other through the electrolyte so as to control oxygen molecules between the air induction section and a gas induction section; a spacer plate having a predetermined thickness and length and provided on the first solid electrolyte; and a second solid electrolyte as a pump section, having a pump anode electrode provided on one surface of the second solid electrolyte and a pump cathode electrode provided on the other surface of the second solid electrolyte.

Another feature of the present invention resides in an air/fuel ratio detecting and controlling apparatus which comprises: the above mentioned air/fuel ratio sensor for detecting air/fuel ratio; a pump current detecting circuit connected to the air/fuel ratio sensor for comparing an output voltage from the sensor with a reference voltage and for detecting change in pump current as change in detection voltage; and a microprocessor having at least a CPU, a ROM, and a RAM, responsive to the detection voltage from the pump current detection circuit as well as to other operated conditions of the engine such as intake air flow rate, throttle valve opening, cooling water temperature, engine speed for performing various operations and calculations so as to detect any normal and abnormal conditions of the air/fuel ratio sensor as well as producing a suitable injection signal for an injector, when the normal condition of the sensor is detected.

Still another feature of the present invention resides in a method of detecting normal and abnormal conditions of the air/fuel ratio sensor, which comprises the steps of: (a) determining if all of cylinders are being injected, the predetermined number of cylinders are being injected, or all of the cylinders are stopped injecting; (b) calculating a correction coefficient A from the following equation in accordance with the result of the determinations;

$$A = \frac{V_3 - V_1}{V_3 - V_2}$$

where
- $V_1$ = detection voltage $V_i$ from a pump current detecting circuit when all cylinders are being injected.
- $V_2$ = the detection voltage $V_i$ when the predetermined number of cylinders are being injected.
- $V_3$ = the voltage $V_i$ when all cylinders are stopped injecting.

(c) comparing an absolute value of $|A-K|$ with a predetermined value of $\alpha$; and (d) determining occurance of an abnormal condition of the air/fuel ratio sensor in accordance with the result of the comparison.

These and other objects, features and advantages of the present invention will be better understood from the following description of the invention with reference with the attached drawings.

DESCRIPTION OF THE PREFERRED EMBODIMENTS

Figure 2:
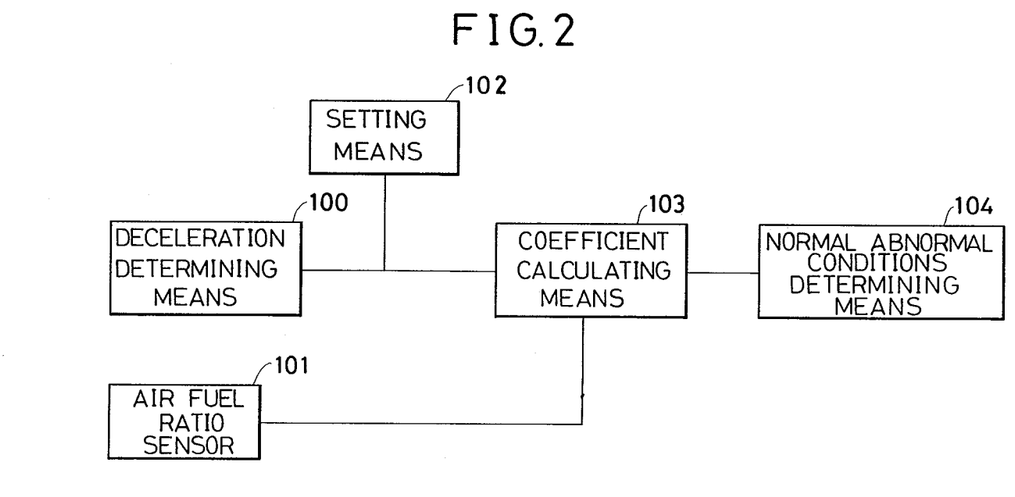
FIG. 2 is a basic concept of the air/fuel ratio detection according to the present invention.

FIG. 2 shows a basic concept of the air/fuel ratio detection. The air/fuel ratio detector comprises deceleration condition determining means 100 for determining the deceleration condition of an engine, an air/fuel ratio sensor 101 for detecting air/fuel ratio of exhaust gas of the engine so as to change fuel injection cylinders to be injected, during deceleration, setting-up means 102 for setting up a supply air/fuel ratio of each cylinder to a predetermined value, coefficient calculating means 103 for calculating a coefficient A in accordance with the following equation, and $$A = \frac{V_3 - V_1}{V_3 - V_2}$$

where
- $V_1$ = detection voltage from the air/fuel ratio sensor when all cylinders are injected.
- $V_2$ = detection voltage from the sensor when the predetermined number of the cylinders
- $V_3$ = detection voltage from the sensor when all of the cylinders are stopped injecting determining means 104 for determining normal and abnormal conditions of the air/fuel ratio sensor in accordance with the coefficient A thus calculated.

The present invention will be described with reference to the drawings. FIG. 3 to FIG. 11 are diagrams for assistance in describing a first embodiment of an air/fuel ratio control apparatus according to the present invention.

Figure 3:
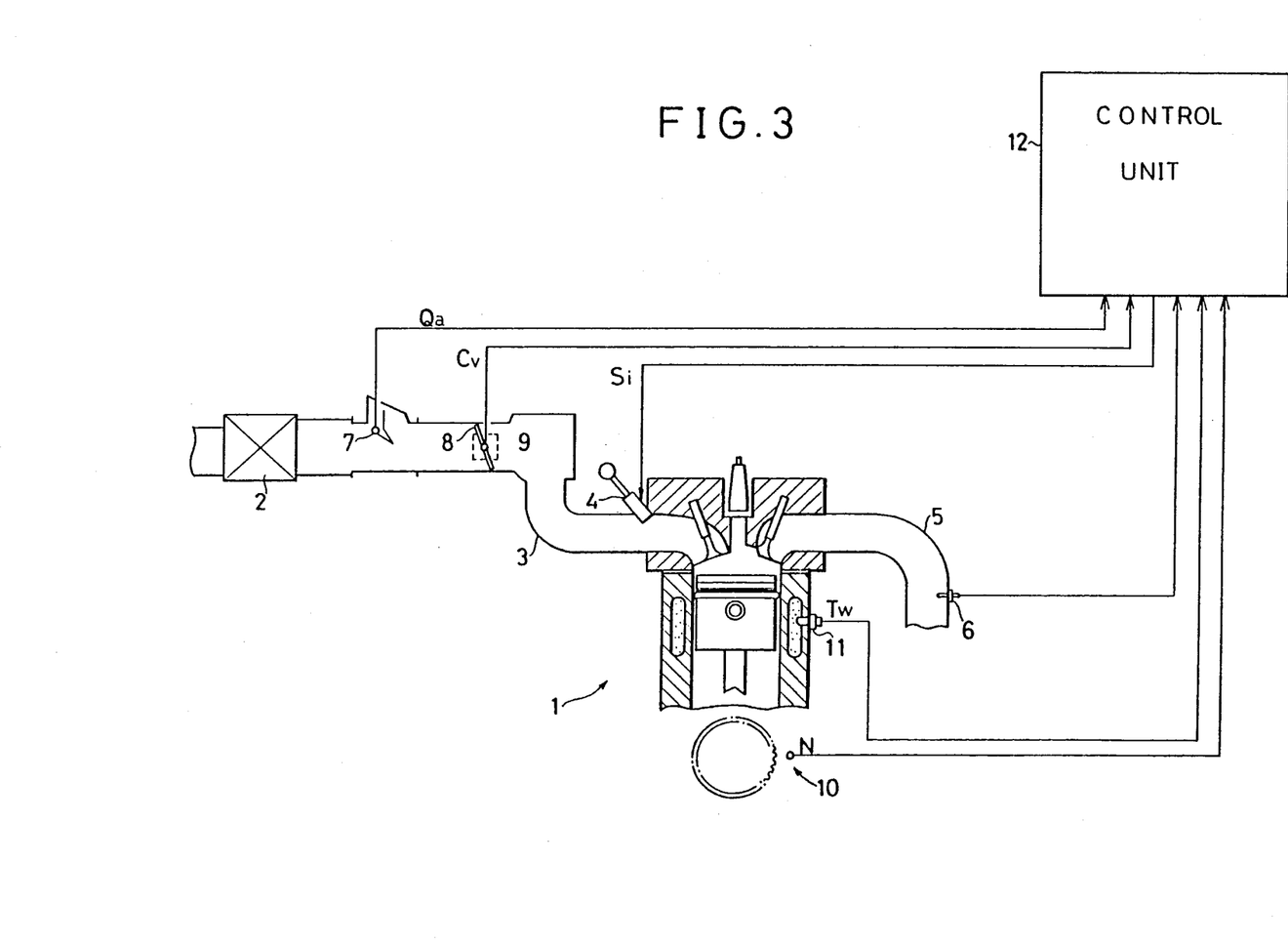
FIG. 3 is an overall construction of the air/fuel ratio detecting and controlling apparatus applied to an engine system, according to the present invention.

The overall configuration will first be described. In FIG. 3, numeral 1 denotes a 4-cylinder engine. Intake air passes through an air cleaner 2 and an air intake pipe 3 to the cylinders. Fuel is injected by an injector 4 in response to an injection signal Si. The exhaust gas from the cylinders is output through an exhaust pipe 5, and the air/fuel ratio in the exhaust gas is detected by an air/fuel ratio sensor 6. The rate of flow Qa of the intake air is measured by an air flow meter 7, and is controlled by a throttle valve 8 in the air intake pipe 3. The angle of opening Cv of the throttle valve 8 is sensed by a throttle opening sensor 9, while the speed of rotation N of engine 1 is detected by a crankshaft angle sensor 10. The temperature Tw of cooling water in the engine water jacket is sensed by a water temperature sensor 11. Signals from the above sensors 6, 7, 9, 10 and 11 are input to a control unit 12, which controls the air/fuel ratio on the basis of data from the sensors. A detailed description of this apparatus will be given letter.

Figure 4:
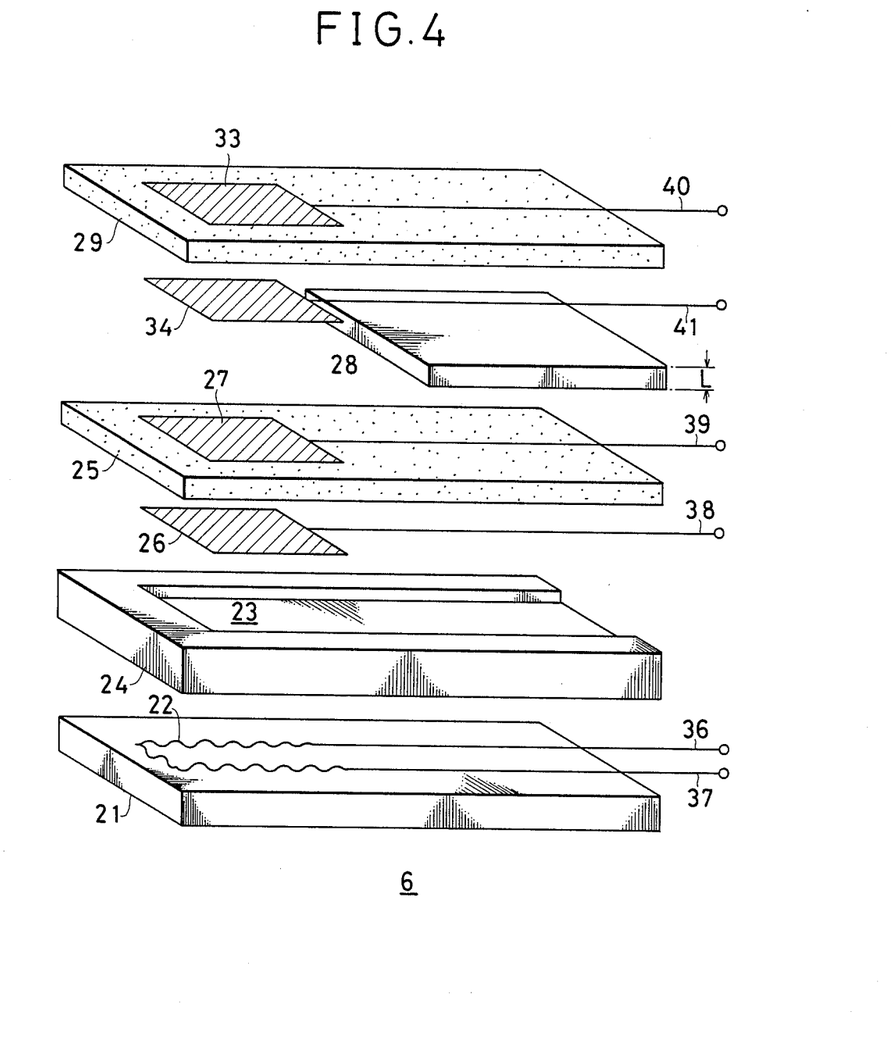
FIG. 4 illustrates a perspective exploded view of the air/fuel ratio sensor according to the present invention.
Figure 5:
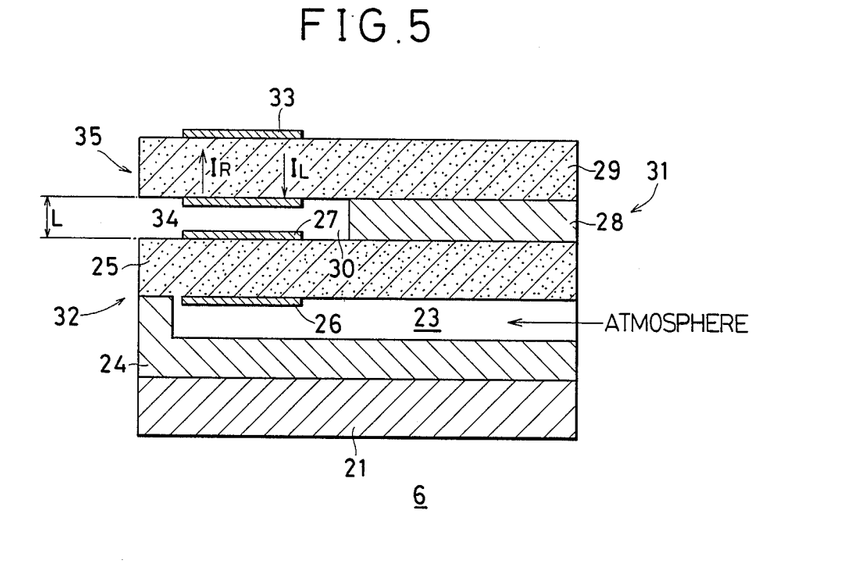
FIG. 5 illustrates a cross-sectional view of the air/fuel ratio sensor according to the present invention.

FIGS. 4 and 5 are an perspective exploded view and a cross-sectional diagram respectively of the air/fuel ratio 6. In FIGS. 4 and 5, numeral 21 denotes a substrate formed of alumina. A heater 22 is mounted on substrate 21, over which is disposed an air induction plate 24 having an air induction section 23 formed thereon in the shape of a channel. A first solid electrolyte 25 in the shape of a flat plate, for providing conduction of oxygen ions, is stacked upon plate 24. A sensor anode (reference electrode) 26 is disposed on the lower face of the solid electrolyte 25, exposed to the atmosphere, while a sensor cathode (measurement electrode) 27, exposed to the exhaust gas, is disposed on the upper face of the solid electrolyte 25 opposite the reference cathode. The sensor anode 26 and sensor cathode 27 are respectively formed by printing. In addition a spacer plate 28 having a thickness l(where l=0.1 mm) is mounted upon the solid electrolyte 25, while a second solid electrolyte 29 formed as a flat plate is disposed upon the spacer plate 28. The solid electrolytes 25 and 29 and spacer 28 thereby cover the sensor cathode 27 and frame a gas induction section (oxygen layer) 30 (see FIG. 5) around the periphery of sensor cathode 27. This oxygen layer enclosure 31 serves to limit the diffusion of oxygen molecules between the exhaust gas and the gas induction section 30. The sensor anode 26, sensor cathode 27 and the first solid electrolyte 25 constitute in combination a sensor section 32. This sensor section 32 produces as output a voltage Vs (hereinafter referred to as the detection voltage) which varies in accordance with the ratio of the partial pressure of oxygen in the air induction section 23 and partial pressure of oxygen in the gas induction section 30.

A pump anode 33 (a pump electrode) is disposed on the upper face of the second solid electrolyte 29, while a pump cathode 34 (pump electrode) is formed on the lower face of solid electrolyte 29. The pump anode 33, pump cathode 34 and the second solid electrolyte 29 constitute a pump section 35, which serves to control the partial pressure of oxygen in the gas induction section 30 in accordance with the value of pump current $I_P$ which flows between the pump electrodes. The sensor section 32, pump section 35, oxygen layer enclosure 31 and the air induction plate 24 constitute in combination an air/fuel ratio sensor 6. The heater 22 heats the solid electrolytes 25 and 29 to a suitable temperature, to thereby activate the electrolytes. Numerals 36 and 37 denote the connecting leads of heater 22, while numerals 38 to 41 respectively denote the lead wires of sensor anode 26, sensor cathode 27, pump anode 33 and pump cathode 34.

Figure 6:
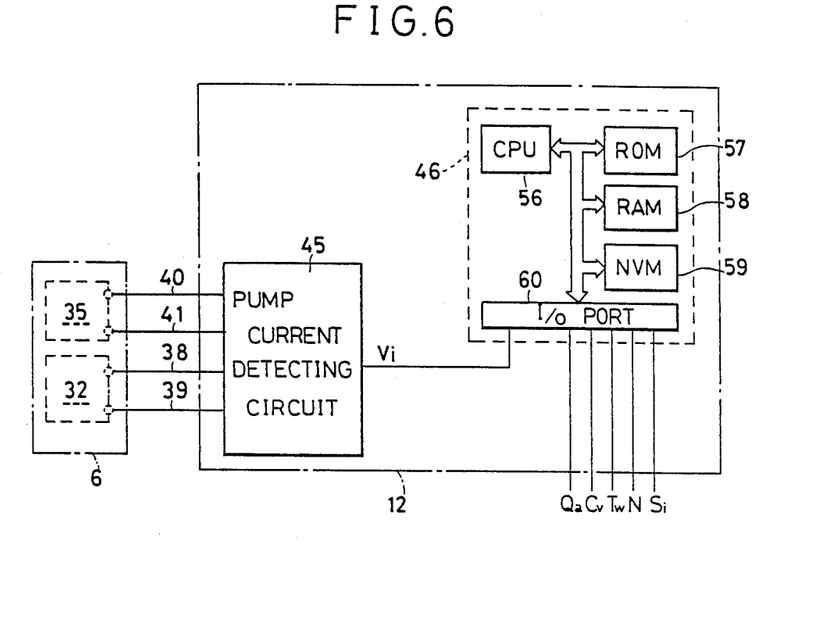
FIG. 6 illustrates the air/fuel ration sensor and a control unit including a pump current detecting circuit connected to the air fuel ratio sensor and a microprocessor, according to the present invention.
Figure 7:
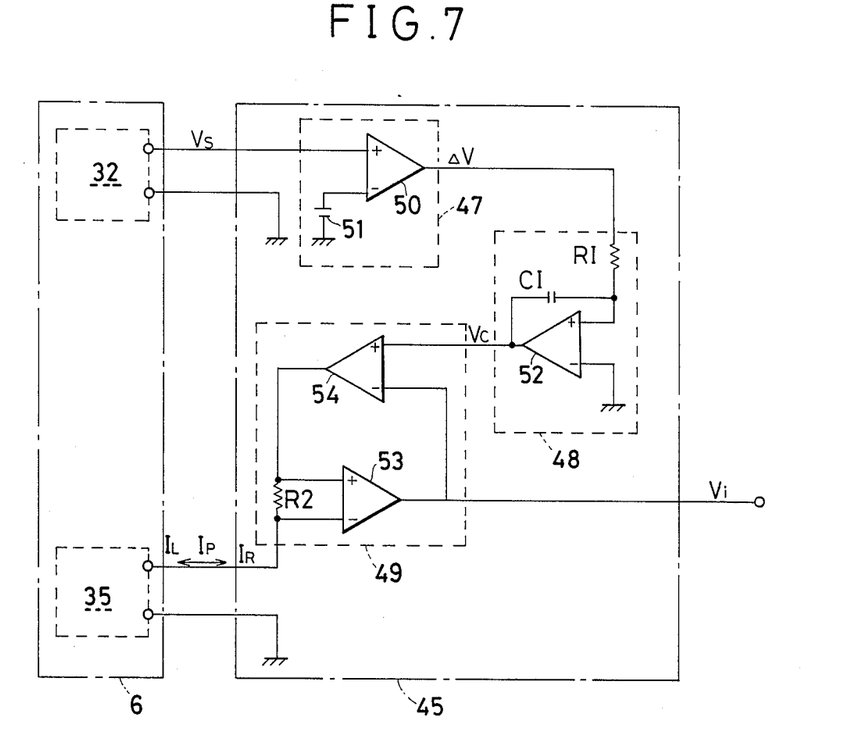
FIG. 7 is a detailed construction of the pump current detecting circuit according to the present invention.

FIG. 6 is a block diagram showing the configuration of control unit 12. In FIG. 6, the control unit 12 is made up of a pump current detection circuit 45 and a microcomputer or microprocessor 46. The pump current detection circuit 45 is shown in detail in FIG. 7. As shown, this circuit is made up of a difference value detection circuit 47, an integrator circuit 48, and a I-V converter circuit 49. The difference value detection circuit 47 is made up of an operational amplifier 50 and a voltage source 51. A target voltage Va is subtracted from the detection voltage Vs, and the resultant difference voltage V is input to an integrator circuit 48. The value of the target voltage Va is determined to be a middle point between the upper and lower limits of the detection voltage Vs, these upper and lower limits being values at which Vs exhibits an abrupt change when the oxygen concentration in the gas induction section 30 is held at a constant level, and this value of Va is set by the voltage source 51. The detection voltage Vs corresponds to the oxygen concentration in the gas induction section 30. Since the target value of voltage Vs corresponds to the predetermined value referred to above, the oxygen value $\Delta V$ represents the magnitude of deviation of the current oxygen concentration in the gas induction section 30 with respect to the predetermined value. The integrator circuit 48 consists of an operational amplifier 52, resistor R1 and capacitor C1, and serves to integrate the deviation voltage $\Delta V$ by a predetermined integration constant, to produce an integration output signal Vc. Signal Vc is input to the I-V converter circuit 49, which is made up of an operational amplifier 54, a differential amplifier 53, and a resistor R2. The I-V converter circuit 49 produces a pump current $I_P$, whose magnitude and direction correspond to the integrator output voltage Vc. In addition, the voltage appearing across the terminals of resistor R2 due to the flow of pump current $I_P$ through that resistor is sensed by amplifier 53, to thereby produce as output a detection voltage $V_i$. The detection voltage $V_i$ takes a positive value when the pump current $I_P$ is in the direction indicated as arrow direction $I_L$ in FIG. 7, and a negative value when the I direction is as indicated by arrow direction $I_R$ (see FIG. 5). Detection voltage $V_i$ therefore directly corresponds to the air/fuel ratio.

More specifically, by supplying a pump current $I_P$ to the air/fuel ratio sensor 6 such that Vs=Va, the partial pressure of oxygen in the gas induction section is determined by the oxygen pumping action of the pump current $I_P$. Assuming the exhaust gas temperature is 1,000° K., then for example if the value of Va is set to 500 mV and the partial pressure of oxygen in the gas induction section (i.e., the partial pressure of oxygen Pb of the sensor cathode 27) is held to a value which is in accordance with the theoretical air/fuel ratio, then this value of Pb is obtained as $0.206 \times 10^{-10}$ atmospheric pressure, from the following Nernst equation (1):

$$E = (RT/4F) \cdot n \cdot (Pa/Pb) \tag{1}$$

Figure 8:
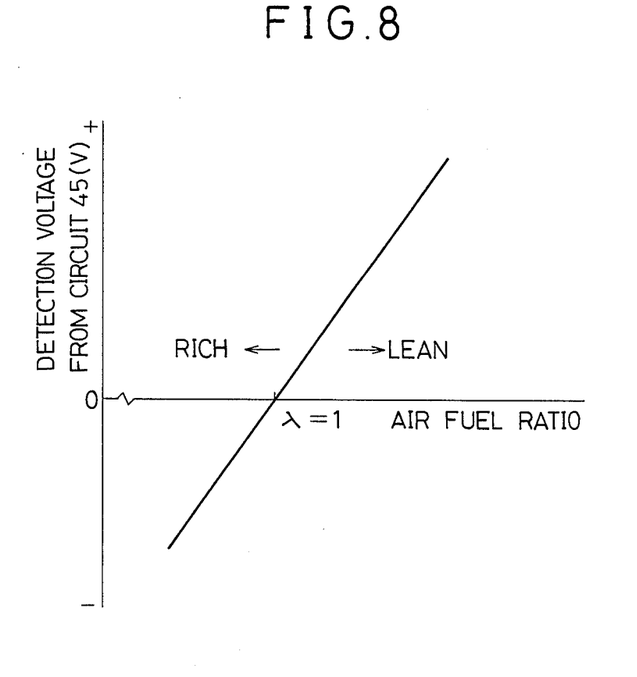
FIG. 8 is the characteristic graph between the detection voltage $V_i$ and air/fuel ratio (A/F)

In the above, R denotes the gas constant, T denotes absolute temperature, F denotes the Faraday constant and P denotes the partial pressure of oxygen of the sensor anode 26. The value $I_P$ of the pump current expresses the magnitude of the energy which is necessary to hold the partial pressure of oxygen Pb at the gas induction section 30 at the aforementioned predetermined value (Pb = $0.206 \times 10^{-10}$ atmospheric pressure), which is in accordance with the theoretical air/fuel ratio, i.e., this value of Pb varies in accordance with changes in the pump current $I_P$. Expressing the relationship between $I_P$ and Pb as the concentration of oxygen in the exhaust gas, and hence as the air/fuel ratio, the $I_P$–A/F characteristic is as shown in FIG. 8. By detecting the level of pump current $I_P$ as the detection voltage $V_i$, continuous measurement of the air/fuel ratio can be carried out. The air/fuel ratio varies in a gradual manner with changes in the detection voltage $V_i$, and is zero for the case of the theoretical air/fuel ratio ($\lambda = 1$), furthermore, when the air/fuel ratio changes from the theoretical air/fuel ratio to the lean air/fuel ration region, then pump current $I_P$ becomes proportional to the value of partial pressure of oxygen in the exhaust gas, while if the air/fuel ratio changes from the theoretical air/fuel ratio to the rich air/fuel ratio region, then the pump current $I_P$ will vary in accordance with the amount of CO or HC, etc, in the exhaust gas. This is due to the fact that these are converted into oxygen molecules, so that the direction of flow of the pump current changes around the theoretical air/fuel ratio i.e., $\lambda = 1$. Thus, the air/fuel ratio can be measured precisely in the rich air/fuel ratio region, and based on this fact, feedback control can be implemented for the rich air/fuel ratio region.

Referring again to FIG. 6, the microcomputer 46 receives the output signals $V_i$, Qa, $C_V$, $T_W$ and N, from the pump current detection circuit 45 and the group of sensors 7, 9, 10 and 11. The microcomputer 46 performs the functions of deceleration conditions judgment means, setting means, coefficient computation means, and determining means and is made up of a CPU 56, a ROM 57, a RAM 58, a NVM (non-volatile data memory) 59, and an I/O port 60. The CPU 56 reads in externally applied data such as Qa, $C_V$, $T_W$, N, through the I/O port 60 in accordance with a program which has been written into the ROM 57, and also performs computation processing while exchanging data with the RAM 58 and the NVM 59, and moreover outputs processed data through I/O port 60 when necessary. The I/O port 60 receives the output signal $V_i$ from the pump current detecting circuit 45 as well as the output signals or data from the group of sensors 7, 9, 10 and 11 as described above and produces as output the fuel injection signal Si, through I/O port 60. The ROM 57 stores operating programs for CPU 56, while RAM 58 and the NVM 59 store data to be used in processing, e.g., in memory-mapped form, etc.

The operation will now be described. Normally, the air/fuel ratio sensor must perform sensing of the high-temperature exhaust gas, and hence must operate in an extremely severe environment. Furthermore, when an air/fuel ratio sensor having a special configuration, such as a sensor which produces a diffusion current (pump current) varying in accordance with the oxygen concentration is employed, then the flow of the diffusion current may become impeded by adherence of extraneous matter to the sensor. In the prior art, such factors have resulting in problems of unreliability of the sensor data.

With the present invention, the air/fuel ratio which is supplied to each engine cylinder is fixed. When the number of cylinders into which fuel is injected is changed, the air/fuel ratio supplied to each cylinder during deceleration is controlled to a constant value, with this control being based on the fact that there is a fixed mutual relationship between the air/fuel ratio in the exhaust gas (i.e., the oxygen concentration in the exhaust gas) and the number of cylinders into which fuel is injected. In addition, during deceleration the detection result obtained from the air/fuel ratio for the condition in which fuel is injected into all cylinders (designated in the present embodiment as the detection voltage $V_i$) and the detection result obtained when fuel is injected only into a specific number of cylinders, together with the detection result obtained when fuel injection into all cylinders is halted, are utilized to compute a coefficient. Any degree of abnormality of the air/fuel ratio sensor is thereby judged, and thereafter the detection results obtained by the air/fuel ratio sensor are appropriately corrected in accordance with this judgment, to thereby provide enhanced accuracy of sensing by the air/fuel ratio sensor.

Figure 9:
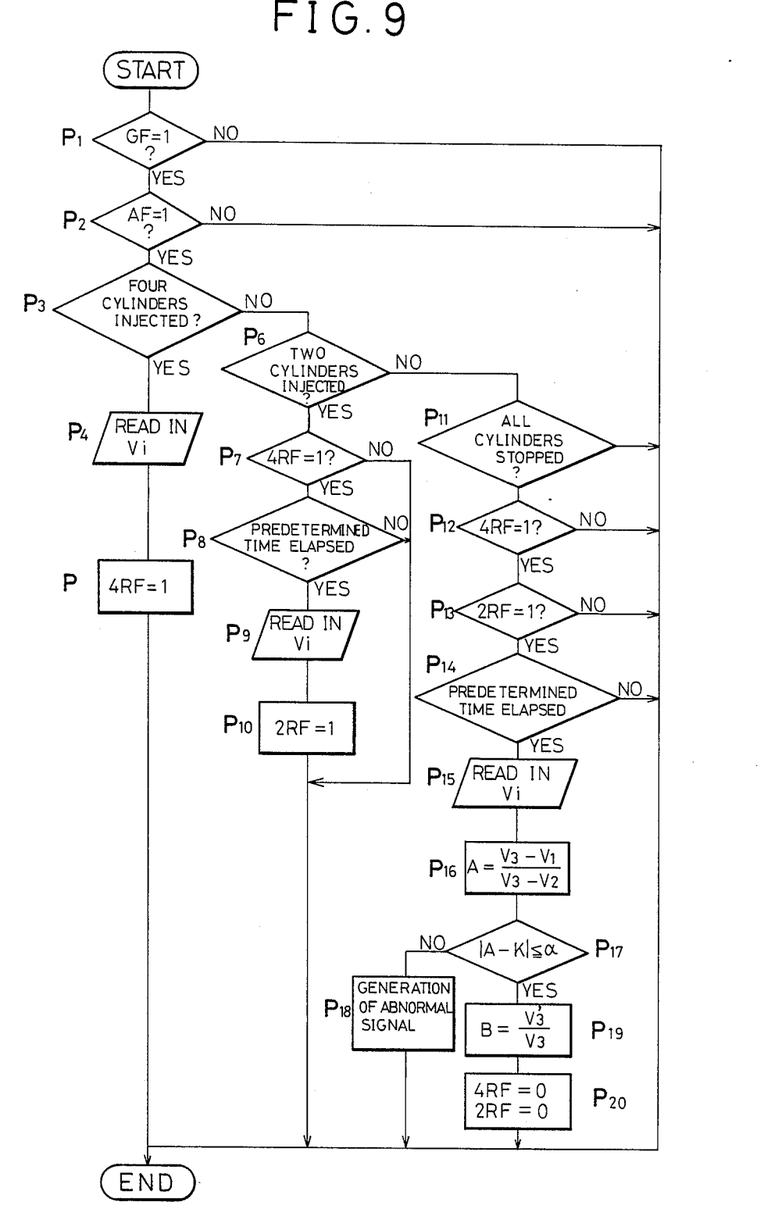
FIG. 9 is a control program flow chart for detecting normal and abnormal conditions of the air/fuel ratio sensor and for correcting the air/fuel ratio, according to the present invention.

A program for computing the above-mentioned coefficient, and a program for judging any sensor abnormality will now be described, referring to the program flow chart of FIG. 9. In FIG. 9, P1 to P20 denote steps in the flow path. First, in step P1, a decision is made as to whether the deceleration flag GF is in the "1" state. The deceleration flag GF is controlled by the main program of microcomputer 46. For example, if the engine speed is higher than 1600 rpm, the cooling water temperature Tw is higher than 65° C., then if the degree of throttle opening as measured by the throttle opening sensor 9 is changed to zero, the system will judge that a deceleration condition has been entered. The deceleration flag GF of RAM 58 will thereby be set to "1" state. If GF="0" in step P1, then this signifies that the deceleration condition has not been entered, and the program flow is ended. If GF="1", then the operation goes to steps P2, where a decision is made as to whether the air/fuel ratio sensor correction flag AF is "1". This air/fuel ratio sensor correction flag AF is controlled by the main program of microcomputer 46. For example after engine 1 has been started, and the output from air/fuel ratio sensor 6 has stabilized, then if the deceleration condition is entered, with air/fuel ratio control halted, the air/fuel ratio correction flag AF of RAM 58 is set to "1", while at the same time the air/fuel ratio is set to a specific fixed value which is appropriate for deceleration operation.

If AF is found to be "0" in step P2, then program execution is ended. If AF="1", then the operation now goes to step P3, where decision is made as to whether fuel injection is being performed into 4 cylinders. Changeover of the number of cylinders into which fuel is injected can be carried out, for example, through the main program of microcomputer 46. It can be arranged for example that if flag GF="1" while flag AF="1", then changeover is performed from 4-cylinder fuel injection operation to 2-cylinder fuel injection operation.

If it is found in step P3 that fuel injection is being performed into 4 cylinders, the operation goes to step P4, where the detection result produced by air/fuel ratio sensor 6 (i.e., the detection voltage $V_i$ from the pump current detection circuit 45) is read in. In step P5, the read-in completion flag 4RF is set to "1" (4RF=1). This indicates that read-in of the detection voltage $V_i$ during 4-cylinder fuel injection operation has been completed. Program execution is then ended. Thus, if the engine has entered the deceleration condition, then when the air/fuel ratio sensor 6 has been activated to a suitable degree, the air/fuel ratio is adjusted to a fixed predetermined value which is appropriate for deceleration operation, while maintaining fuel injection to 4 cylinders, and the detection voltage $V_i$ from the pump current detection circuit 45 is read in.

Next, in step P3, a decision is made as to whether fuel is being injected into all cylinders. If not, then in step P6 a decision is made as to whether fuel injection into only two cylinders is being performed. If the decision is "YES", then in step P7 a decision is made as to whether the read-in completion flag 4RF is "1". That is to say, a decision is made as to whether reading of the detection voltage $V_i$ has been completed, for the case when fuel is injected into all cylinders. If flag 4RF is found to be "0" in step P7, then since this indicates that the detection voltage $V_i$ during fuel injection into 4 cylinders has not been read in, the program flow is ended. If flag 4RF="1" in step P7, the operation now moves to step P8, where a decision is made as to whether a predetermined time interval has elapsed since changeover from fuel injection into 4 cylinders to fuel injection into 2 cylinders. If this predetermined time interval has not elapsed, then program execution is ended. This predetermined time interval is determined based on the speed of rotation N of the engine, and the air intake flow rate Qa, and corresponds to the time taken for the exhaust gas (used to measure the air/fuel ratio) to reach the air/fuel ratio sensor 6 after changeover has been performed to fuel injection into 2 cylinders.

If the predetermined time interval is found to have elapsed in step P8, then in step P9 the detection voltage $V_i$ for fuel injection into 2 cylinders is read in. In step P10, the read-in completion flag 2RF is set to "1" (2RF="1" ), to indicate that the detection voltage $V_i$ during fuel injection into 2 cylinders has been read in, and program execution is ended.

If it is judged in step P6 mentioned above that fuel injection into 2 cylinders is not in progress, the operation goes to step P11, where a decision is made as to whether fuel injection into all cylinders is halted. If this is not true, then program execution is ended. If fuel injection into all cylinders is halted, then in steps P12 and P13 decisions are respectively made as to whether the read-in completion flags 4RF and 2RF have been set to "1". That is to say, a decision is made as to whether the detection voltage $V_i$ has been read in both during fuel injection into 4 cylinders and during fuel injection into 2 cylinders. If both of flags 4RF and 2RF are not set to the "1" state, then program execution is ended, leaving the states of these flags unchanged. If flag 4RF="1" and 2RF="1" in steps $P_{12}$ and $P_{13}$, then the operation goes to step P14, where a decision is made as to whether a predetermined time interval has elapsed since changeover from fuel injection into 2 cylinders to the condition in which fuel injection into all cylinders is halted. If this predetermined time interval has not elapsed then program execution is ended with the states of these flags left unchanged. If the predetermined time interval has elapsed, then in step P15, the detection voltage $V_i$ during operation with fuel injection into all cylinders is halted (i.e., for the condition in which the exhaust gas has the same constituents as air) is read in. In step P16, the coefficient A is computed from the detection voltage $V_i$ ($=V_1$) obtained during fuel injection into 4 cylinders (i.e., when fuel is injected into all cylinders), the detection voltage $V_i$ ($=V_2$) obtained during fuel injection into 2 cylinders (i.e., during operation when fuel is injected only into a predetermined number of cylinders), and the detection voltage $V_i$ ($=V_3$) obtained when fuel injection into all cylinders is halted. The coefficient A is computed from the following equation:

$$A = (V_3 - V_1) / (V_3 - V_2) \quad (1)$$

Figure 10:
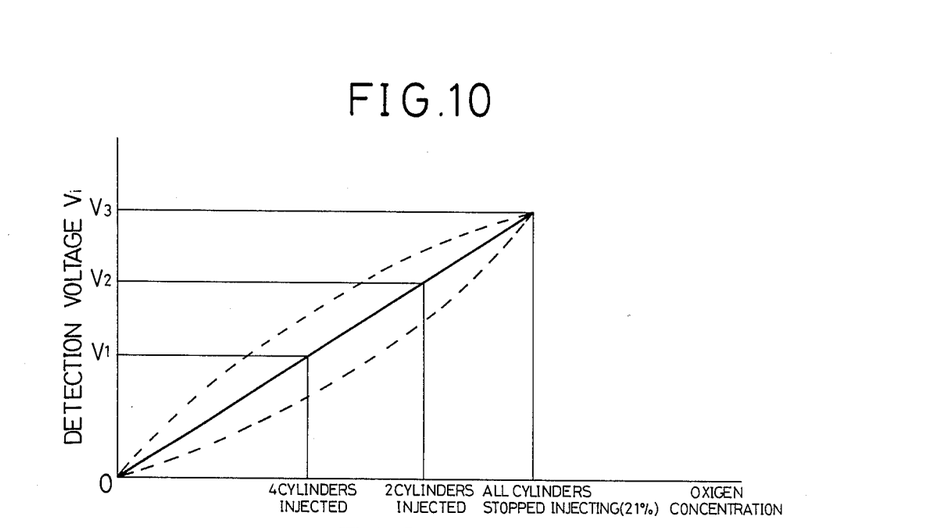
FIG. 10 illustrates a relationship between the detection voltage $V_i$ and oxygen concentration.

If the output characteristic of the air/fuel ratio sensor 6 is linear, as shown by the full-line portion in FIG. 10, then the coefficient A will be equal to the ratio K, which is the ratio of the total number of cylinders (i.e., the number applicable when fuel is injected into all cylinders) to the aforementioned predetermined number of cylinders (i.e., when fuel is injected only into a specific number of cylinders). If, however, the output characteristic of air/fuel ratio sensor 6 is non-linear, as shown by the broken-line portion of FIG. 10, then the coefficient A will differ from the ratio K. That is to say, taking the condition with fuel injection into all cylinders is halted as a reference condition, the rate of oxygen consumption during operation when fuel is injected into all cylinders (i.e., in the present embodiment, fuel injection into 4 cylinders) will be K times the rate of oxygen consumption during operation when fuel is injected only into a predetermined number of cylinders (i.e., with the present embodiment, operation with fuel injection into two cylinders). With the present embodiment, therefore K=2. Thus, if the air/fuel ratio sensor 6 has a linear output characteristic, the coefficient A will be equal to K, where A is the ratio of the value ($V_3-V_1$) obtained by subtracting the detection voltage $V_1$ for operation during fuel is injected into all cylinders from the detection voltage $V_3$ obtained for operation when fuel injection into all cylinders is halted, to the value ($V_3-V_2$), where $V_2$ is the detection voltage obtained when fuel is injected only into a predetermined number of cylinders.

In step P17 a decision is made as to whether the absolute value $|A-K|$ obtained from the coefficient A and the ratio K is less than a predetermined value. If $|A-K|$ is greater than this is taken as indicating that the non-linearity of the air/fuel ratio sensor 6 is outside acceptable limits, an hence in step P18 a warning signal is generated to indicate this unacceptable level of sensor abnormality. This warning signal may for example consist of the lighting of a warning lamp, or emission of a buzzer sound. If, however, the result of the decision in step P17 is YES, the operation goes to step P19, where a correction factor B is computed, and then the operation now moves to step P20, where the read-in completion flags 4RF and 2RF are set to the "0" state (4RF="0", 2RF="0"). B is computed from the following equation:

$$B = V_3'/V_3 \quad (2)$$

In the above, $V_3'$ is the initial value of the detection voltage obtained from the air/fuel ratio sensor when the sensor is first set in operation in the atmospheric condition.

Figure 11:
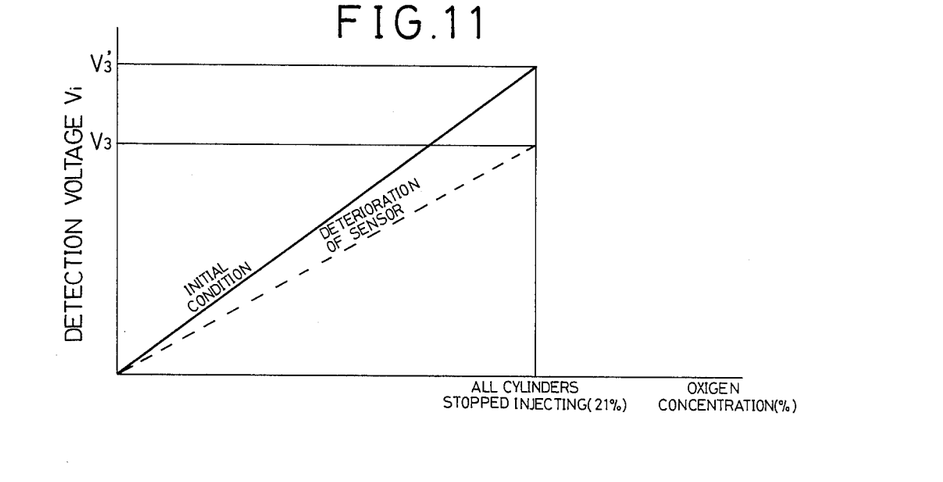
FIG. 11 illustrates another relationship between the detection voltage and oxygen concentration for correction of the air/fuel ratio.

As shown in FIG. 11, the correction factor B expresses the amount of deterioration of air/fuel ratio sensor 6, if the output characteristic of sensor 6 is held linear. The detection voltage $V_i$ obtained from the pump current detecting circuit 45 can, thus, be appropriately corrected by the correction factor B, if the sensor maintains a linear output characteristic.

As described above, a decision is made as to whether the linearity of the output characteristic of air/fuel ratio sensor 6 is within acceptable limits. If the linearity is outside these limits, then a warning indication of abnormal is issued, and no correction of the detection voltage $V_i$ obtained from circuit 45 is performed. If the linearity is judged to be within acceptable limits, however, then the detection voltage $V_i$ from sensor 6 through the detection circuit 45 is corrected on the basis of the sensor output voltage produced when air is passed through the sensor. In this way, abnormality of sensor 6 can be rapidly dealt with when it arises, while when sensor 6 is functioning normally, suitable correction of the detection voltage $V_i$ can be implemented. Thus the air/fuel ratio can be accurately detected, and can be, thereby, controlled to a precisely desired target value.

Figure 12:
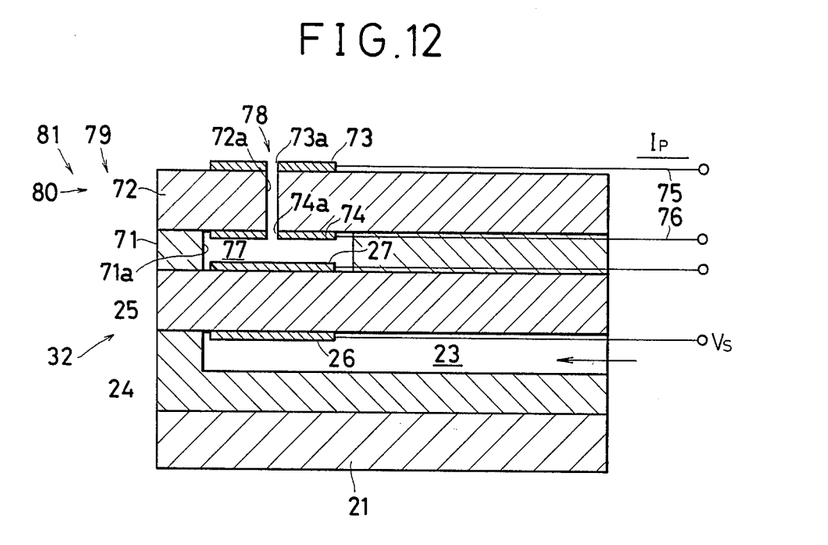
FIG. 12 illustrates a second embodiment of the air/fuel ratio sensor according to the present invention.

FIG. 12 is a diagram of an air/fuel ratio sensor according to a second embodiment of the present invention, having a modified configuration. In FIG. 12, a partitioning plate 71 is sandwiched between a first solid electrolyte 25 and a second solid electrolyte 72, with solid electrolyte 72 being disposed on the upper face of partitioning plate 71. A small aperture 72a is formed in the solid electrolyte 72, while a large rectangular through-aperture 71a is formed in the partitioning plate 71. A pump anode 73 is formed as a layer on the upper face of solid electrolyte 72, while a pump cathode layer 74 is formed on the lower face of solid electrolyte 72, with the pump anode and pump cathode being enclosed within the through-aperture 71a and with the pump cathode 74 and pump anode 73 being positioned concentric with the small aperture 72a in solid electrolyte 72. Small apertures 73a and 74a are respectively formed in the pump anode 73 and pump cathode 74, coaxial with through-aperture 72a. In addition, connecting leads 75 and 76 are respectively coupled to the pump anode 73 and pump cathode 74. The solid electrolyte 72 and partitioning plate 71 cover and surround the periphery of sensor cathode 27, to configure a gas induction section (oxygen layer) 77. The exhaust gas is led past solid electrolyte 72 in an upward direction as viewed in the drawing. The small apertures 72a to 74a constitute in combination a diffusion aperture 78, which communicates between the exhaust gas and the gas induction section 77. The partitioning plate 71 and the solid electrolyte 72 constitute an oxygen layer enclosing section 79, which serves to limit the diffusion of oxygen molecules between the exhaust gas and the gas induction section 77. In other respects, this embodiment is identical to that of FIG. 2.

The solid electrolyte 72, pump anode 73 and pump cathode 74 in combination constitute a pump section 80. The pump section 80, sensor section 32, oxygen layer enclosure 79 and air induction plate 24 in combination constitute an air/fuel ratio sensor 81.

It can be understood from the above that with the present invention, the partial pressure of oxygen in the gas induction section 77 is set to a value which corresponds to the theoretical air/fuel ratio, by supplying a pump current $I_P$ such that Vs becomes equal to Va. As a result, the air/fuel ratio can be detected within wide limits, by detecting the level of pump current $I_P$ from the value of detection voltage $V_i$. In addition, the present invention is also applicable to an air/fuel ratio sensor such as sensor 81, with identical results to those described previously being obtainable.

The above embodiments have been described for the case of an engine having four cylinders, however, it should be noted that the invention is not limited to this number of cylinders. Furthermore, in the above embodiments the predetermined number of cylinders into which fuel injection is performed is 2. However, the predetermined number of cylinders is not limited to that value. Essentially, the present invention enables variations in the output from the air/fuel ratio sensor to be clearly recognized, for a system in which the air/fuel ratio is to be held constant and the number of cylinders into which fuel is injected is to be varied. Based on these changes in the output of the air/fuel ratio sensor, the effects of deterioration of the sensor can be ascertained.

The present invention enables discrimination between normal and abnormal operation of an air/fuel ratio sensor, and hence, enables appropriate measures to be taken when the sensor is found to be abnormal. In addition, when the sensor is operating normally, appropriate correction of the detection results produced by the sensor can be performed, to thereby, enhance the accuracy of control of the engine air/fuel ratio.

While the invention has been described in its preferred embodiments, it is to be understood that the words which have been used are words of description rather than limitation and that various changes and modification may be made within the purview of the appended claims without departing from the true scope and spirit of the invention in its broader aspects.

What is claimed is:

1. An air/fuel ratio detecting and controlling apparatus which comprises:
    an air/fuel ratio sensor for detecting air/fuel ratio of exhaust gas from an engine and having a sensing section outputting a voltage in accordance with oxygen concentration in the air/fuel ratio sensor;
    a pump current means for changing a pump current supplied to the air/fuel ratio sensor;
    a pump current detecting circuit connected to said air/fuel ratio sensor for comparing an output voltage from said sensing section with a reference voltage and for detecting a change in pump current as a change in detection voltage ($V_i$); and
    detecting means for detecting any normal and abnormal conditions of said air/fuel ratio sensor according to the detection voltage ($V_i$) from said pump current detecting circuit.

2. An air/fuel ratio detecting and controlling apparatus as claimed in claim 1, wherein said detecting means calculates a correction coefficient (A) from the following equation in accordance with the result of the determinations;

$$A = \frac{V_3 - V_1}{V_3 - V_2}$$

where
$V_1$ = the detection voltage $V_i$ when all cylinders are being injected,
$V_2$ = the detection voltage $V_i$ when the predetermined number of cylinders are being injected,
$V_3$ = the voltage $V_i$ when all cylinders are stopped injecting, compares an absolute value of $|A-K|$ with a predetermined value of $\alpha$; and determines occurrence of an abnormal condition of the air/fuel ratio sensor in accordance with the result of the comparison.

3. An air/fuel ratio detecting apparatus as claimed in claim 1, wherein said detecting means detects any normal and abnormal conditions of said air/fuel ratio sensor as well as produce a suitable injection signal for an injector when the normal condition of the sensor is detected, according to the detection voltage ($V_i$) from said pump current detecting circuit as well as to other operated conditions of the engine such as intake air flow rate ($Q_a$), throttle valve opening ($C_v$), cooling water temperature ($T_w$), engine speed (N).

4. An air/fuel ratio detecting apparatus as claimed in claim 1, wherein said air/fuel ratio sensor comprises:
    a substrate having a heater provided thereon;
    an air induction plate having an air induction section and provided on said substrate;
    a first solid electrolyte as a sensor section, having an anode electrode provided on one surface of said first solid electrolyte and a cathode electrode provided on the other surface of said electrolyte face-to-face each other through said electrolyte so as to control oxygen molecules between the air induction section and gas induction section;
    a spacer plate having a predetermined thickness and length and provided on said first solid electrolyte; and
    a second solid electrolyte as a pump section, having a pump anode electrode provided on one surface of said second solid electrolyte and a pump cathode electrode provided on the other surface of said second solid electrolyte.

5. An air/fuel ratio detecting and controlling apparatus as claimed in claim 4, wherein said substrate is made of alumina.

6. The air/fuel ratio detecting and controlling apparatus as claimed in claim 5 wherein numerical data corresponding to the steps of the method as claimed in claim 1 have preliminarily been stored in the ROM.

7. An air/fuel ratio detecting apparatus as claimed in claim 4, wherein the thickness l of said spacer plate is l=0.1 mm.

8. An air/fuel ratio detecting apparatus as claimed in claim 4, wherein said second solid electrolyte has a diffusion hole penetrating through the pump anode electrode and the pump cathode electrode substantially in the center of said two electrodes and an additional spacer having the same thickness as that of the first spacer is provided at the other end of said first and second electrolytes so as to surround said cathode electrode and said pump cathode electrode.

9. An air/fuel ratio detecting apparatus as claimed in claim 1, wherein the length of said spacer plate is approximately half of that of first and second solid electrolytes so as not to contact said cathode electrode and said pump cathode.

10. The method of detecting normal and abnormal conditions of of an air/fuel ratio sensor as claimed in claim 9, wherein the total number of cylinder injection is four cylinders.

11. The method as claimed in claim 9, wherein the predetermined number of cylinder injection is two cylinders.

12. A method of detecting normal and abnormal conditions of the air/fuel ratio sensor, which comprises the steps of:
(a) determining if all cylinders are being injected, the predetermined number of cylinders are being injected, or all of the cylinders are stopped injecting;
(b) calculating a correction coefficient from the following equation in accordance with the result of the determinations;

$$A = \frac{V_3 - V_1}{V_3 - V_2}$$

where
$V_1$=the detection voltage $V_i$ when all cylinders are being injected,
$V_2$=the detection voltage $V_i$ when the predetermined number of cylinders are being injected,
$V_3$=the voltage $V_i$ when all cylinders are stopped injecting,
(c) comparing an obsolete value of : A−K : with a predetermined value of α determined on the basis of linearity of the output characteristics of the air/fuel ratio sensor where K is the ratio of the number of all the cylinders to the predetermined number of cylinders; and
(d) determining occurrence of an abnormal condition of the air/fuel ratio sensor in accordance with the result of the comparison.

13. A method of detecting normal and abnormal conditions of an air/fuel ratio sensor, which comprises the steps of:
(a) determining if a deceleration flag is set at "1";
(b) determining if a correction flag is set at "1" in accordance with the result of said first determination;
(c) determining if all of cylinders in question are being injected in accordance with the result of said second determination after detecting an all cylinder injected condition;
(d) setting a first read-in completion flag (4RF) to "1";
(e) maintaining the above condition, i.e., all cylinder injected condition,
(f) adjusting the air/fuel ratio to a constant value; and
(g) detecting a detection voltage ($V_i$) from a pump current detecting circuit.

14. The method of detecting normal and abnormal conditions of an air/fuel ratio sensor, as claimed in claim 13 wherein the method further comprises the steps of:
(h) determining if the predetermined number of cylinders less than the total number of cylinders are being injected in accordance with the result of the determination performed in step c;
(i) determining if the first read-in completion flag (4RF) is set at "1" in accordance with said fourth determination;
(j) determining if a predetermined time has elapsed after switching from the all cylinder injected condition to the predetermined number of cylinder injected condition; and
(k) setting a second read-in completion flat (2RF) to "1" after detecting the predetermined number of cylinder injected condition.

15. The method of detecting an abnormal condition of an air/fuel ratio sensor as claimed in claim 14, wherein it further comprises the steps of:
(l) determining if all of the cylinders are stopped injecting in accordance with the determination performed in step (j);
(m) determining if the first and second read-in flags are set at "1" respectively in accordance with the determination performed in step (l);
(n) determining if a predetermined time has elapsed after switching from the predetermined number of cylinder injected condition to the all cylinder injected condition in accordance with the determination performed in step (m);
(o) calculating a coefficient A according to the following equation after detecting the various cylinder operated and stopped conditions;

$$A = \frac{V_3 - V_1}{V_3 - V_2}$$

where
$V_1$ indicates the detection voltage ($V_1$) in the all cylinder injected condition
$V_1$ indicates the detection voltage ($V_1$) in the all cylinder injection stopped condition
$V_3$ indicates the detection voltage ($V_i$) in the all cylinder injection stopped condition;
(p) determining if an absolute value of $|A-K|$ is equal to or smaller than a predetermined value of α, in accordance with the result of the calculation in step
(o); where K indicates ratio of the two cylinder injected conditions; and
(q) generating a sensor abnormal signal when the determination in step (p) is not affirmative, i.e., $|A-K|>α$ in accordance with the result of the determination in step (p).

16. The method as claimed in claim 15, wherein it further comprises:
(r) calculating an auxiliary coefficient B from the following equation when the determination in step (p) is affirmative, i.e., $|A-K|≦α$; and $B=V_3'/V_3$ where $V_3'$ indicates the detection voltage ($V_i$) during the initial operation of the air/fuel ratio sensor in the atmospheric condition,
(s) setting each of the read-in completion flags (4RF 2RF) to "0" respectively, in accordance with the result of the calculation in step (r).

17. The method as claimed in claim 16, wherein it further comprises the step of correcting the detection signal ($V_i$) from the pump current detecting circuit as long as the output signal maintains linearity in accordance with the result of the calculation of the auxiliary coefficient.

18. An air/fuel ratio sensor detecting apparatus which comprises:
(a) deceleration condition determining means for determining the deceleration condition of an engine;
(b) an air/fuel sensor for detecting air/fuel ratio of exhaust gas of the engine;
(c) means for changing the number of fuel injection cylinders to be injected during deceleration;
(d) setting-up means for setting up a supply air/fuel ratio of each cylinder to a predetermined value;
(e) coefficient calculating means for calculating a coefficient A in accordance with the following equation; and $$A = \frac{V_3 - V_1}{V_3 - V_2}$$

where
$V_1$ = detection voltage ($V_i$) from the pump current detection circuit when all cylinders are being injected,
$V_2$ = the detection voltage of the pump current detection circuit when the predetermined number of cylinders are being injected,
$V_3$ = the detection voltage of the detection circuit when all of the cylinders are stopped injecting; and
(f) determining means for determining normal/abnormal conditions of the air/fuel ratio sensor in accordance with the coefficient A, thus, calculated.

* * * * *